United States Patent [19]

McEwen

[11] Patent Number: 5,352,195

[45] Date of Patent: * Oct. 4, 1994

[54] APPARATUS FOR INTRAVENOUS REGIONAL ANESTHESIA

[75] Inventor: James A. McEwen, Richmond, Canada

[73] Assignee: IVRA Systems, Inc., Vancouver, Canada

[*] Notice: The portion of the term of this patent subsequent to Oct. 19, 2010 has been disclaimed.

[21] Appl. No.: 935,785

[22] Filed: Aug. 27, 1992

Related U.S. Application Data

[63] Continuation-in-part of Ser. No. 471,514, Jan. 29, 1990, Pat. No. 5,254,087.

[51] Int. Cl.⁵ .............................................. A61M 31/00
[52] U.S. Cl. ....................................... 604/66; 606/202; 128/677; 128/DIG. 12
[58] Field of Search ................... 604/30, 31, 65–67; 606/201–203; 128/677, 686, 783, 744, DIG. 12, DIG. 13

[56] References Cited

U.S. PATENT DOCUMENTS

| | | | |
|---|---|---|---|
| 3,164,152 | 1/1965 | Vere Nicoll | 128/87 |
| 3,319,623 | 5/1967 | London | 604/66 |
| 4,168,063 | 9/1979 | Rowland | 273/54 B |
| 4,321,929 | 3/1982 | Lemelson | 128/630 |
| 4,469,099 | 9/1984 | McEwen . | |
| 4,479,494 | 10/1984 | McEwen . | |
| 4,533,346 | 8/1985 | Cosgrove, Jr. et al. | 604/66 |
| 4,605,010 | 9/1986 | McEwen . | |
| 4,635,635 | 1/1987 | Robinette-Lehman . | |
| 4,667,672 | 5/1987 | Romanowski . | |
| 4,718,891 | 1/1988 | Lipps | 604/31 |
| 4,770,175 | 9/1988 | McEwen . | |
| 4,781,189 | 11/1988 | Vijil-Rosales . | |
| 4,869,165 | 9/1989 | McEwen | 128/774 |
| 5,048,536 | 9/1991 | McEwen | 128/748 |
| 5,103,833 | 4/1992 | Apple | 128/687 |
| 5,108,363 | 4/1992 | Tuttle et al. | 604/20 |
| 5,181,522 | 1/1993 | McEwen | 606/203 |
| 5,254,087 | 10/1993 | McEwen | 604/66 |

OTHER PUBLICATIONS

C. M. Holmes, "Intravenous Regional Neural Blockade," in Neural Blockade, M. J. Cousins & P. O. Bridenbaugh, Eds., pp. 443–459, J. B. Lippincott & Co., 1988.

ECRI, "Pneumatic Tourniquets used for Intravenous Regional Anesthesia", Health Devices, Dec. 1982, pp. 48–49.

S. C. Grice et al., "Intravenous Regional Anesthesia: Prevention of Leakage . . . ", Anesthesiology, vol. 65, pp. 316–320, 1986.

(List continued on next page.)

Primary Examiner—Ralph Lewis
Attorney, Agent, or Firm—Klarquist Sparkman Campbell Leigh & Whinston

[57] ABSTRACT

Apparatus for assisting in the administration of anesthesia in a portion of a patient's limb distal to a cuff comprises in combination: applied pressure transducing means for generating an applied pressure signal representative of a pressure applied to a limb by a cuff which encircles the limb and applies pressure to the limb; anesthetic pressure sensing means for sensing the pressure of anesthetic liquid in a vein distal to the cuff and for generating an anesthetic liquid pressure signal indicative of the pressure; and alarm means for producing an alarm signal when the difference between the pressures corresponding to the applied pressure signal and the anesthetic liquid pressure signal is less than a preassigned safety limit. The apparatus may include anesthetic control means responsive to the alarm signal for stopping the introduction of anesthetic liquid when the difference is less than a preassigned limit, anesthetic concentration sensing means for estimating the concentration of anesthetic liquid in the blood, and anesthetic level estimation means for estimating the level of anesthesia in the portion of the limb distal to the cuff.

18 Claims, 1 Drawing Sheet

OTHER PUBLICATIONS

J. A. H. Davies et al., "Intravenous Regional Analgesia: Danger of the Congested Arm and the Value of Occlusion Pressure", Anaesthesia, 1983, vol. 39, pp. 416–421.

E. M. Brown et al., "Intravenous Regional Anesthesia (Bier Block): Review of 20 Years' Experience," Can. J. Anaesth., 1989, vol. 36, pp. 307–310.

J. Haasio, "Intravenous Regional Anesthesia of the Arm: Effect of the Technique of Exsanguination . . . ", Anaesthesia, vol. 44, pp. 19–21, 1989.

C. Sorbie and P. Chacha, "Regional Anaesthesia By The Intravenous Route," Brit. Med. J., 1965, 1, 957–960.

K. M. El-Hassan et al., "Venous Pressure and Arm Volume Changes During Simulated Bier's Block", Anesthesia, 1984, 39:229–235.

B. A. Finegan & M. D. Bukht, "Venous Pressures in the Isolated Upper Limb . . . ", Can. Anaes. Soc. J., 1984, 31:364-7.

R. Sukhani et al., "Lidocaine Disposition . . . With Different Tourniquet Deflation Technics," Anesth. Analg. 1989, 68:633–7.

W. L. Lehman et al., "Intravenous Lidocaine for Anesthesia in the Lower Extremity," J. B. J. S. 66-A, 1984, pp. 1056–1060.

J. H. Davies & A. J. Walford, "Intravenous Regional Anesthesia For Foot Surgery," Acta. An. Scand., 1986, 30:145–147.

L. N. Nusbaum, "IVRA For Surgery on the Foot and Ankle," Anesthesiology, 64:91–92, 1986.

G. S. Dunean, "The Use of IVRA in Podiatric Surgery," J. Foot Surg., vol. 25, 1986, pp. 411–415.

J. Duggan et al., "Venous Pressures in IVRA," Reg. Anes., 9:70–72, 1984.

T. A. Hoel, "Prevention of Leak of Local Anesthetic From Under a Pneumatic Tourniquet," Anesthes., 66:449–458, 1987.

H. Finlay, "A Modification of Bier's Intravenous Analgesia," Anaesthesia, 1977, 357–358.

APPARATUS FOR INTRAVENOUS REGIONAL ANESTHESIA

REFERENCE TO RELATED APPLICATION

This is a continuation in part of U.S. patent application Ser. No. 07/471,514, filed Jan. 29, 1990 now U.S. Pat. No. 5,254,087.

FIELD OF THE INVENTION

This invention pertains to improved apparatus for use in intravenous regional anesthesia, a technique for anesthetizing a portion of a limb to facilitate surgery. In particular, the invention pertains to automated apparatus for automatically controlling the introduction, retention and release of anesthetic liquid in a portion of the limb distal to a pressurizing cuff.

BACKGROUND OF THE INVENTION

This invention pertains to apparatus for automating the administration and management of intravenous regional anesthesia (IVRA) for both upper and lower limbs. IVRA is an alternative to general anesthesia for limb surgery. IVRA has proven to be a simple and useful technique for satisfactorily anesthetizing the upper limb and is potentially well suited for greatly expanded utilization in surgery of lower limbs and in outpatient settings. In these settings, which are rapidly increasing in number worldwide, there is a large and unmet need for a rapid, simple, safe and reliable technique for establishing limb anesthesia. However, significant practical problems with the technology of IVRA in the prior art, considerable variations in skill involving the manual administration of IVRA, and lingering concerns over the potential toxicity of certain IVRA agents, particularly for lower limbs, have greatly limited the acceptance of this promising technique.

IVRA is an anesthetic technique which requires the use of a surgical pneumatic tourniquet ststem. Surgical pneumatic tourniquet systems are frequently used on the upper and lower limbs to help maintain a bloodless operative field by regulating the maximum pressure applied to the limb by an encircling cuff at a pressure sufficient to stop arterial blood flow past the cuff for the duration of a surgical procedure. During operations performed under IVRA, the pneumatic tourniquet serves an additional role of preventing liquid anesthetic agent introduced into the veins in the limb distal to the cuff from flowing proximally past the cuff and out of the limb into the circulatory system. An insufficient pressure in the tourniquet cuff soon after introduction of the liquid anesthetic agent into the limb may result in the anesthetic agent entering the circulatory system in a high concentration, which can cause serious adverse reactions such as cardiovascular collapse, respiratory depression, epileptic seizures or even death.

IVRA is typically administered as follows. The limb is first exsanguinated, often by wrapping the limb with an elastic bandage, beginning distally and wrapping tightly towards the heart; after exsanguination, a tourniquet cuff is applied proximal to the operative site and inflated to a predetermined cuff pressure. The elastic bandage is removed and a liquid anesthetic agent such as lidocaine mixed with sterile saline is introduced into a vein in the limb through an intravenous cannula. The anesthetic liquid remains in the veins in the limb distal to the cuff as long as the tourniquet is inflated to a sufficient pressure. Premature release of the agent shortly after introduction, as well as leakage of the agent under the cuff during introduction or during surgery, are serious and recognized hazards associated with prior art devices used for IVRA.

Surgical tourniquet systems of the prior art typically include an inflatable cuff for encircling a limb and an automatic pressure regulator for maintaining the pressure to which the cuff is inflated near a reference pressure selected by an operator or determined automatically. Recently, research and clinical investigations were completed with an improved surgical tourniquet system which incorporated a novel biomedical pressure transducer disclosed by McEwen in U.S. Pat. No. 4,869,269. The novel transducer was positioned underneath the cuff to measure the pressure distribution applied by the cuff to the limb at a number of discrete locations relative to the cuff. Experiments revealed that normal variations in technique used to apply the cuff to the limb were found to vary the maximum pressure actually applied to the limb by 50 percent or more, in comparison to the regulated bladder pressure of the cuff. This variability has important implications for IVRA, especially with regard to the potentially serious and recognized hazard of premature release or leakage of the liquid anesthetic agent proximally past the cuff and into the general circulation.

There are also specific hazards associated with the use of prior art tourniquet systems for IVRA because there has been little or no monitoring of maximum pressure actually applied to the limb by the cuff, the pressure at which anesthetic liquid is injected, and the increased pressure in the veins due to introduction of the anesthetic liquid. Injection of the anesthetic liquid at a high pressure has been shown to lead to excessive pressures in the veins distal to the tourniquet cuff, which in some cases has led to anesthetic liquid flowing past the cuff and into general circulation. Similarly, because of variations in cuff types and application techniques, despite an appropriately chosen cuff inflation pressure, the maximum pressure actually applied to the limb by the cuff may be significantly less than the regulated pneumatic bladder pressure indicated on the tourniquet pressure display; in this case, injection of anesthetic liquid at only a moderate pressure may increase the pressure in the veins above the pressure actually applied by the cuff so that anesthetic liquid flows proximally past the cuff. Both of the above-described situations can lead to an ineffective regional anesthesia in general, and to increased hazards, including cardiac arrest and death in a small number of reported cases.

Another hazard associated with the use of IVRA is related to the release of the anesthetic liquid from the limb upon completion of the surgical procedure. Although cyclical cuff deflation and re-inflation protocols requiring manual operation of tourniquets for predetermined periods and pressures at the completion of surgery have been recommended in the prior art, no apparatus for automatic cycling of cuff deflation and inflation has been implemented in the prior art, and in many clinical situations the anesthetic liquid is simply released from the limb in a single bolus by fully deflating the tourniquet cuff at the completion of surgery. The reported incidence of toxic reactions to post-operative release of the anesthetic liquid from the limb is approximately 2 percent, the majority of the reactions being manifested typically within one minute of tourniquet release as minor, temporary disturbances of the central nervous system (CNS) such as giddiness, dizziness, or tinnitus (ringing in the ears) and in some cases minor bradycardia (reduction in heart rate). More serious phenomena, such as muscle twitching, convulsions, and loss of consciousness have been reported at an incidence of approximately 0.2 percent in cases in which the anesthetic agent was lidocaine. Convulsions have been reported in many cases in which bupivicaine has been used. Nothing in the prior art known to the applicant has suggested control of the tourniquet apparatus based on monitored physiological changes arising from to the release of anesthetic liquids, despite the present availability of techniques for non-invasively observing physiological changes associated with the reported symptoms of CNS toxicity.

A related hazard is that the administering anesthetist generally is unable to detect or monitor any possible leakage of the anesthetic agent during a surgical procedure involving the use of IVRA. The prior art does not describe, mention or suggest apparatus for monitoring the concentration of anesthetic liquid in blood proximal to the cuff, or distal to the cuff, during IVRA. The recent development of transcutaneous, intra-arterial and intravenous transducers for estimating anesthetic concentration by a variety of direct and indirect approaches has made this feasible.

Another hazard recognized in use of IVRA is related to the volume of liquid anesthetic introduced into the limb, particularly in the case of procedures performed on the lower extremity in which a larger volume of liquid anesthetic may be required. In the prior art, this factor, combined with concerns over potential toxicity has been the primary limitation preventing extension of IVRA to many lower limb procedures. Protocols described in the prior art have largely specified which agents, volumes, and concentrations for given clinical situations are appropriate. Despite the potentially larger toxic hazards associated with larger volumes of anesthetic agent, the applicant in unaware of any recommendation in the prior art concerning IVRA which suggests that the volume of liquid anesthetic delivered be a function of the level of anesthesia produced in a portion of the limb distal to the cuff, even althought clinical experiments were conducted in the prior art in which the level of anesthesia during IVRA was related to conventional electromyographic determinations of motor nerve conduction velocity.

In summary, IVRA has proven to be a simple and useful technique for satisfactorily anesthetizing the upper limb and is potentially well suited for greatly expanded utilization in surgery of lower limbs and in outpatient settings. However, significant practical problems with the technology of IVRA in the prior art and lingering concerns over the potential toxicity of certain IVRA agents have greatly limited the acceptance of this promising technique. Despite potential complications associated with leakage of anesthetic liquid proximally under the cuff, the applicant is unaware of any apparatus in the prior art which alerts the administering anesthetist by means of an alarm, or which prevents leakage of anesthetic liquid by means of anesthetic control means, in response to monitoring and estimation of the maximum pressure actually applied to the limb by the cuff and the pressure of the anesthetic liquid introduced into the limb distal to the cuff. Prevention of toxic reactions to post-operative anesthetic release have not, to the applicant's knowledge, been addressed in the prior art by controlling the tourniquet in response to the concentration of the anesthetic liquid in the patient's body proximal to the cuff. The applicant is also unaware of any apparatus described in the prior art in which anesthetic control means responsive to the level of anesthesia introduces sufficient anesthetic liquid to establish a level of anesthesia near a predetermined level, thereby preventing the introduction of an unnecessary and potentially hazardous volume of drug.

An object of the present invention is to provide apparatus for assisting in the administration of IVRA, including a transducer for producing a signal representative of the maximum pressure applied to the limb by a cuff encircling the limb, a transducer for producing a signal indicative of the anesthetic liquid pressure within a vein of the limb distal to the cuff, and an alarm which is activated when the difference between the applied pressure signal and the anesthetic liquid pressure signal is less than a preassigned safety limit, to alert the administering anesthetist and thereby prevent inadvertent leakage of anesthetic liquid under the cuff. A related object of the present invention is to include apparatus for stopping the introduction of anesthetic liquid when the alarm is activated.

Another object of the present invention is to provide apparatus for administering anesthesia to a portion a limb distal to a cuff, including a transducer for producing a signal representative of a pressure applied to the limb by a cuff encircling the limb, means for delivering the anesthetic liquid into a vein in the limb and for producing a delivery pressure signal indicative of the delivery pressure, and an alarm which is activated when the difference between the applied pressure signal and the delivery pressure signal is less than a preassigned safety limit to alert the administering anesthetist and thereby prevent leakage of anesthetic liquid under the cuff.

A further object of the present invention is to provide apparatus for the containment and release of anesthetic liquid from a limb encircled by a pressurizing cuff which restricts flow of anesthetic liquid proximally past the cuff, including means for controlling the pressure applied by the cuff to the limb and means for estimating the concentration of the anesthetic liquid in the patient's body proximal to the cuff. A related object of the present invention is to provide control means which restricts flow proximally past the cuff to keep the concentration of anesthetic liquid below a preassigned concentration limit so that CNS toxicity is avoided. A further related object is to include an alarm which is activated if the estimated concentration exceeds a preassigned safety limit, to warn of impending toxicity.

Another object of the present invention is to provide apparatus for establishing a desired level of anesthesia in a portion of a limb distal to a pressurizing cuff which encircles the limb, including means for estimating the level of anesthesia in the portion of the limb distal to the cuff, and anesthetic control means responsive to the estimated level of anesthesia which activates anesthetic delivery means to introduce sufficient anesthetic liquid to result in a level of anesthesia near a predetermined level, thereby preventing the introduction of an unnecessary and potentially hazardous volume of liquid anesthetic agent. A related object of the invention is to include an alarm which is activated when the level of anesthesia exceeds a preassigned safety limit.

SUMMARY OF THE INVENTION

The invention is directed toward apparatus for assisting in the administration of anesthesia in a portion of a patient's limb distal to a cuff, comprising in combination: applied pressure transducing means for generating an applied pressure signal representative of a pressure applied to a limb by a cuff which encircles the limb and applies pressure to the limb; anesthetic pressure sensing means for sensing the pressure of anesthetic liquid in a vein distal to the cuff and for generating an anesthetic liquid pressure signal indicative of the pressure; and alarm means for producing an alarm signal when the difference between the pressures corresponding to the applied pressure signal and the anesthetic liquid pressure signal is less than a preassigned safety limit. The apparatus may include anesthetic delivery control means responsive to the alarm signal for stopping the introduction of anesthetic liquid when the difference is less than a preassigned limit.

The invention is further directed toward apparatus for controlling the containment and release of anesthetic liquid in a vein of a patient's limb distal to a pressurizing cuff comprising: a pressurizing cuff for substantially encircling a limb and applying pressure to a vein in the encircled limb to restrict flow past the cuff proximally of anesthetic liquid contained in a vein from the portion of the limb distal to the cuff; anesthetic concentration sensing means for estimating the concentration of anesthetic liquid in blood and for producing an anesthetic concentration signal indicative of the concentration; and cuff pressure control means responsive to the anesthetic concentration signal for controlling the pressure applied by the cuff to the limb. The apparatus may include alarm means to generate an alarm signal when the concentration represented by the anesthetic concentration signal exceeds a preassigned concentration safety limit.

The invention is also directed toward apparatus for establishing a desired level of anesthesia in a portion of a limb, comprising: a pressurizing cuff for substantially encircling a limb and applying pressure to a vein in the encircled limb to restrict flow past the cuff proximally of liquid in the vein in the portion of the limb distal to the cuff; anesthetic drug delivery means responsive to an anesthetic delivery signal for introducing an anesthetic liquid into a vein distal to the cuff; anesthetic level estimation means for estimating a level of anesthesia in the limb and for producing an anesthetic level signal representative of the level of anesthesia; and anesthetic control means responsive to the anesthetic level signal for producing an anesthetic delivery signal which results in the introduction of a volume of anesthetic liquid sufficient to establish a level of anesthesia near a predetermined level.

DESCRIPTION OF THE PREFERRED EMBODIMENT

Figure 1:
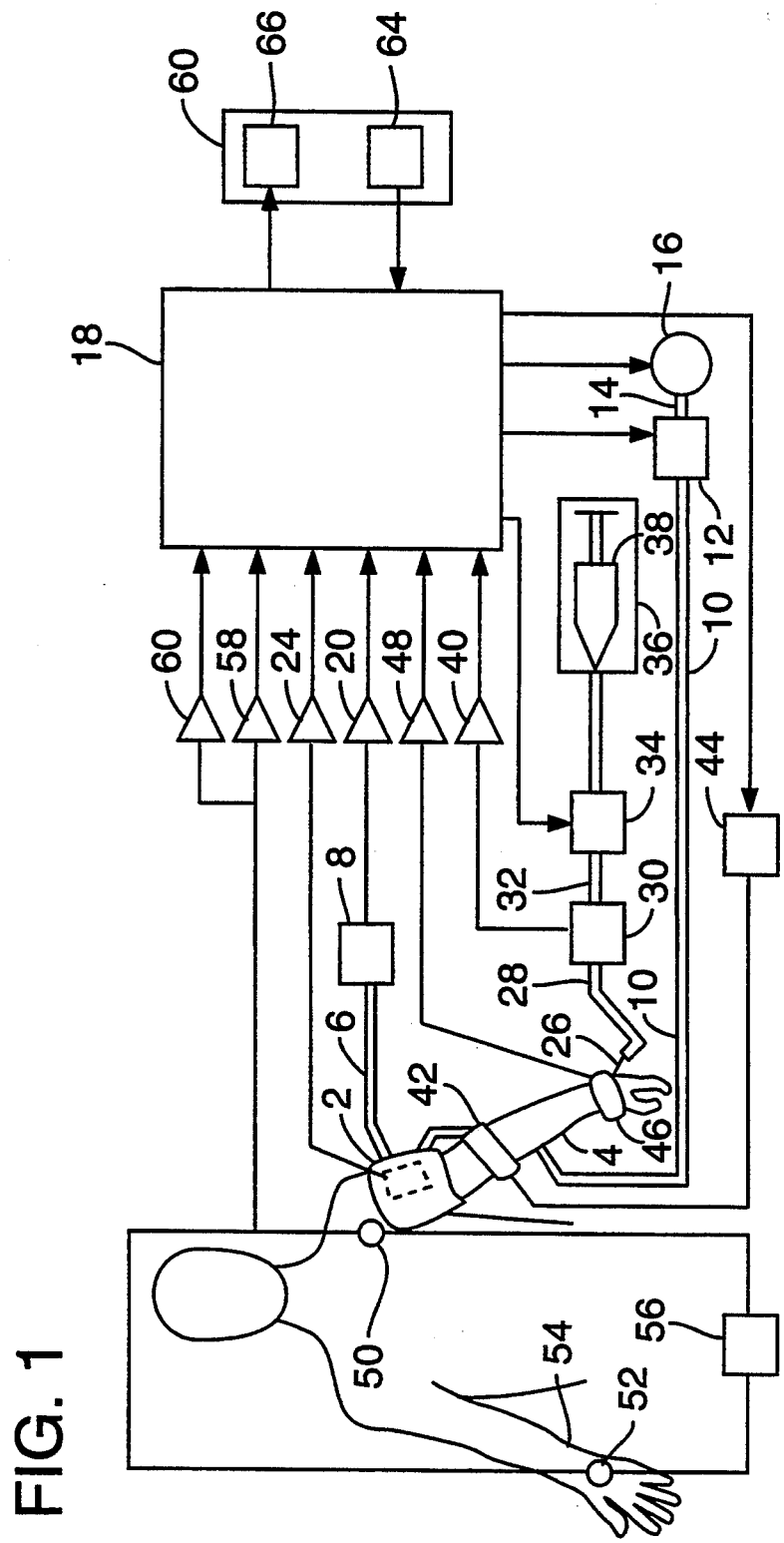

The embodiment illustrated is not intended to be exhaustive or to limit the invention to the precise form disclosed. It is chosen and described in order to explain the principles of the invention and its application and practical use, and thereby enable others skilled in the art to utilize the invention.

Illustrated in FIG. 1 is automatic apparatus for assisting in the administration of anesthesia to a portion of a patient's limb distal to a cuff. Referring to FIG. 1, pressurizing cuff 2 substantially encircles and applies pressure to operative limb 4, and is connected by tubing 6 to pressure transducer 8 (Spectramed 072911-000-583, Spectramed Inc., Oxnard Calif.). Cuff 2 is also connected by tubing 10 to deflation valve 12 (Clippard EVO-3-12V, Clippard Instrument Laboratory, Cincinnati Ohio), which connects through tubing 14 to diaphragm air pump 16 (Neuberger PU67-05-11.83, K. F. Neuberger Inc., Princeton N.J.). Pump 16 is activated by an inflation control signal from integrated digital processor 18 (Intel 80C196, Intel Corp., Santa Clara Calif.) for inflating cuff 2 from zero pressure up to a maximum of 500 mmHg, and valve 12 is activated by a deflation control signal from processor 18 for deflating cuff 2 to zero pressure. Processor 18 incorporates analog-to digital converter, random access memory, read-only memory, and digital input-output ports integrated on a single LSI substrate. Pressure transducer 8 produces an inflation pressure signal representative of the pressure of gas in cuff 2, and the inflation pressure signal from transducer 8 is processed by signal conditioner 20 and communicated to the analog-to-digital converter of processor 18. Transducer 8, valve 12, pump 16 and processor 18 thereby form cuff pressure control means for controlling the pressure applied by cuff 2 to limb 4. This control is functionally accomplished through an algorithm executed by processor 18 and which is described subsequently.

Applied pressure transducer 22, such as the biomedical pressure transducer disclosed by McEwen in U.S. Pat. No. 4,869,265, is located underneath cuff 2. Applied pressure transducer 22 produces an applied pressure signal representative of the maximum pressure applied by cuff 2 to limb 4. The applied pressure signal from transducer 22 is processed by signal conditioner 24 and communicated to processor 18.

Cannula 26 is inserted in a vein in limb 4 distal to cuff 2 and is connected through tubing 28 to pressure transducer 30 (Spectramed 072911-000-583, Spectramed Inc., Oxnard Calif.). Pressure transducer 30 is connected by tubing 32, which passes through solenoid-operated pinch valve 34 (Acro 951-12-L-21-25, Acro Associates, Concord Calif.), to syringe infusion pump 36 (Harvard series 900, Harvard Apparatus Co., Millis Mass.). Clamped into syringe pump 36 is syringe 38 (Monoject 60 cc, Sherwood Medical Co., St. Louis Mo.), which is filled with anesthetic liquid, such as 40 mL of 0.5% lidocaine in physiological saline. Syringe pump 36 is activated by an anesthetic delivery signal produced by processor 18 for introducing the anesthetic liquid into the vein in limb 4, and solenoid valve 34 provides anesthetic control means for stopping the introduction of the anesthetic liquid. If solenoid valve 34 is open and anesthetic liquid pressurized by syringe pump 36 is flowing through it, pressure transducer 30 produces a delivery pressure signal indicative of the pressure at which liquid is introduced into the vein in limb 4. The delivery pressure signal from transducer 30 is processed by signal conditioner 40 and communicated to processor 18. If solenoid valve 34 is closed and anesthetic liquid is prevented from flowing through it, pressure transducer 30 is isolated from syringe pump 36 and is connected by the static fluid column contained in tubing 28 and cannula 26 to the vein in limb 4. Transducer 30 thereby produces an anesthetic liquid pressure signal indicative of the pressure of anesthetic liquid in the vein in limb 4 distal to cuff 2. The anesthetic liquid pressure signal from transducer 30 is similarly processed by signal conditioner 40 and communicated to processor 18.

Stimulating band 42 is wrapped around limb 4 at a predetermined location distal to cuff 2 overlying a large, superficial motor nerve in limb 4, for example, at the position of the antecubital fossa overlying the median nerve of limb 4. In practice, stimulating band 42 may be fabricated from two pediatric-sized electrocardiogram electrodes (3M "Red dot" pediatric, 3M Health Care Systems, St. Paul Minn.) glued to a Velcro strap. Stimulating band 42 is connected to current pulse generator 44, which in turn is activated by a stimulation control signal from processor 18 to stimulate a motor nerve in limb 4. Detecting band 46 is wrapped around limb 4 at a predetermined location distal to band 42 overlying a muscle which contracts in response to electrical stimulation from band 42, for example, overlying the thenar muscle of limb 4. In practice, detecting band 46 may be fabricated from two pediatric-sized electrocardiogram electrodes (3M "Red dot" pediatric, 3M Health Care Systems, St. Paul Minn.) glued to a Velcro strap. Detecting band 46 produces a stimulation response signal indicative of the response of limb 4 to electrical stimulus from band 42. The stimulation response signal from band 46 is processed by signal conditioner 48 and communicated to processor 18. Stimulating band 42, detecting band 46, and processor 18 thereby form anesthetic level estimation means for estimating the level of anesthesia in the portion of limb 4 distal to cuff 2. This estimation is functionally accomplished through an algorithm executed by processor 18 which is described subsequently.

Chlorided silver electrode 50 is applied to the chest of the patient immediately inferior to the clavicle, and chlorided silver electrode 52 is applied contralaterally to the palmar surface of the hand of non-operative limb 54. Electrodes 50 and 52 are connected to current source 56, which produces a constant direct current of approximately 25 microamperes. The signal from electrodes 50 and 52 is processed by signal conditioner 58 and signal conditioner 60. Signal conditioner 58 amplifies frequencies in the range 0.1 to 100 Hz and produces a lead-II electrocardiogram (ECG) signal which is communicated to processor 18. Signal conditioner 60 amplifies frequencies in the range 0.03 to 5 Hz and produces a skin resistance change (SRC) signal which is communicated to processor 18. Electrodes 50 and 52, generator 56, signal conditioners 58 and 60, and processor 18 thereby form means for estimating the concentration of anesthetic fluid in the blood in the patient's body proximal to cuff 2. This estimation is functionally accomplished through an algorithm executed by processor 18 which is described subsequently.

The user communicates with the apparatus of FIG. 1 by means of user panel 62. Switches 64 on user panel 62 are used to input information and commands from the user to processor 18, and processor 18 reports pressures, system status, and alarms to the user by audio-visual display 66.

In operating the apparatus of FIG. 1, the user first applies cuff 2, transducer 22, and electrodes 50 and 52 to the patient and introduces cannula 26 into a superficial vein in limb 4. The user then exsanguinates limb 4 using a clinically accepted technique and instructs processor 18 by means of switches 64 on panel 62 to inflate cuff 2 to a predetermined reference pressure to apply pressure to limb 4 sufficient to occlude blood flow into limb 4.

Control of the gas pressure within cuff 2 is accomplished through execution of the following algorithm.

Processor 18 produces an inflation control signal which activates pump 16 to introduce air into cuff 2 by means of tubing 10. The inflation pressure signal produced by transducer 8 is monitored by processor 18, and when the difference between the predetermined reference pressure and the inflation pressure signal falls within a predefined pressure window of $\pm 3$ mmHg, processor 18 stops producing the inflation control signal which inhibits pump 16. Thereafter, processor 18 samples the inflation pressure signal from transducer 8 once every 100 msec as determined by a timer-driven interrupt internal to processor 18 and communicates the value of the inflation pressure to the user by means of display 66 on panel 62. If, at any given sample instant, the difference between the inflation pressure signal and the predefined reference pressure exceeds $+3$ mmHg, processor 18 produces a deflation control signal which activates valve 12 for 20 msec to incrementally reduce the gas pressure within cuff 2. Similarly, if at any given sample instant the difference between the inflation pressure signal and the predefined reference pressure falls below $-3$ mmHg, processor 18 produces an inflation control signal which activates pump 16 for 50 msec to incrementally increase the gas pressure within cuff 2. In this manner, the algorithm executed by processor 18 regulates the gas pressure within cuff 2 within a predefined pressure window of $\pm 3$ mmHg about the predetermined reference pressure.

Following inflation of cuff 2, the user instructs processor 18 by means of switches 64 on panel 62 to administer anesthesia in the portion of limb 4 distal to cuff 2. Processor 18 produces both an anesthetic delivery signal which activates syringe pump 36 and an anesthetic control signal which opens pinch valve 34, thereby delivering anesthetic liquid through tubing 32, tubing 28 and cannula 26 to the vein in limb 4 at a flow rate of approximately 50 cc/minute. Processor 18 monitors transducer 22 underneath cuff 2 which produces an applied pressure signal representative of the pressure applied to the vein in limb 4 by cuff 2, and also monitors transducer 30 which produces a delivery pressure signal indicative of the pressure at which anesthetic liquid is being introduced into the vein. If the difference between the pressures corresponding to the applied pressure signal and the delivery pressure signal is less than the preassigned safety limit of 100 mmHg, processor 18 produces an audio-visual alarm signal to the user by means of display 66 on panel 62.

Once every 800 msec during delivery of the anesthetic liquid into limb 4 distal to cuff 2, processor 18 stops producing the anesthetic delivery signal which inhibits syringe pump 36, and produces an anesthetic control signal to close pinch valve 34. Flow through transducer 30 thus stops, and processor 18 samples the anesthetic liquid pressure signal from transducer 30 which indicates the pressure of anesthetic liquid in the vein of limb 4 distal to cuff 2. Processor 18 also samples the applied pressure signal produced by transducer 22 underneath cuff 2. If the difference between the pressures corresponding to the applied pressure signal and the anesthetic liquid pressure signal is less than the preassigned safety limit of 30 mmHg, processor 18 produces an audio-visual alarm signal to the user by means of display 66 on panel 62. This alarm signal also causes processor 18 to maintain pinch valve 34 in the closed state, thereby stopping the introduction of the anesthetic liquid when difference between the pressures corresponding to the applied pressure signal and the anesthetic liquid pressure signal is less than the preassigned limit of 30 mmHg.

The apparatus of FIG. 1 establishes a desired level of anesthesia in the portion of limb 4 distal to cuff 2 by means of the following algorithm executed by processor 18. As described previously, the user instructs processor 18 by means of switches 64 on panel 62 to administer anesthesia in the portion of limb 4 distal to cuff 2. While processor 18 produces the anesthetic delivery signal which activates syringe pump 36 to introduce anesthetic liquid into the vein in limb 4 distal to cuff 2, processor 18 also produces a stimulation control signal at a rate of 0.5 Hz which activates current generator 44 to stimulate limb 4 with current pulses by means of band 42. Processor 18 monitors the stimulation response signal from detecting band 46, and produces an anesthetic level signal representative of the level of anesthesia in the portion of limb 4 distal to cuff 2. The anesthetic level signal produced by processor 18 is inversely proportional to the stimulation response signal, and is directly proportional to the increase in the difference between the time of the stimulation response signal and the time of the stimulation control signal. Processor 18 monitors the anesthetic level signal and continues to produce the anesthetic delivery signal until sufficient anesthetic liquid is introduced to result in a level of anesthesia near a predetermined level. In practice, processor 18 accomplishes this by producing the anesthetic delivery signal until the time difference between the response and control signals increases by a predefined percentage of 30%, or the response signal falls below a predetermined threshold near zero. If the level of anesthesia represented by the anesthetic level signal exceeds a preassigned safety limit, processor 18 produces an audio-visual alarm signal to the user by means of display 66 on panel 62. Processor 18 also monitors the duration of time that the anesthetic delivery signal is active, and stops producing the anesthetic delivery signal after approximately 50 seconds when syringe pump 36 has discharged 40 cc of anesthetic liquid from syringe 38.

After a desired level of anesthesia has been established in the portion of limb 4 distal to cuff 2, the user removes cannula 26, band 42, and band 46, and the surgical procedure commences. Following completion of the surgical procedure, the anesthetic liquid retained within the portion of limb 4 distal to cuff 2 may be released.

The apparatus of FIG. 1 controls the containment and release of anesthetic liquid in the vein of limb 4 distal to cuff 2 by means of the following algorithm executed by processor 18. Upon completion of the surgical procedure, the user instructs processor 18 by means of switches 64 on panel 62 to release the anesthetic liquid from limb 4. Processor 18 produces an anesthetic release signal which causes valve 12 to deflate cuff 2 to zero pressure for 10 seconds, and then causes pump 16 to pressurize cuff 2 such that the inflation pressure signal from transducer 8 approaches a predetermined reference pressure which is sufficient to occlude blood flow into limb 4 for 30 seconds. Processor 18 controls the pressure applied to limb 4 by cuff 2 by repeating this deflation and inflation cycle as long as the anesthetic release signal remains active. Processor 18 estimates the concentration of anesthetic liquid in the blood in the patient's body proximal to cuff 2 by monitoring the electrocardiogram (ECG) signal from signal conditioner 58 and the skin resistance change (SRC) signal from signal conditioner 60. Toxic reactions to the anesthetic liquid in the patient's blood stream may produce cardiovascular responses such as bradycardia, or symptoms such as giddiness, dizziness and tinnitus which may be accompanied by an autonomically-induced skin response, specifically, a change in skin resistance. Hence, processor 18 produces an anesthetic concentration signal which is directly proportional to the amplitude of the SRC signal and inversely proportional to the rate of the ECG signal.

During release of the anesthetic liquid from limb 4, processor 18 continues to produce an anesthetic release signal, which results in periodic deflation and re-inflation of cuff 2, until the SRC signal exceeds a predefined threshold or the rate of the ECG signal decreases by more than the predefined threshold of 15 beats per minute; under these conditions, processor 18 inhibits the anesthetic release signal for a period of two minutes and maintains the pressure applied by cuff 2 to limb 4 so that anesthetic liquid is contained within limb 4. Processor 18 thus permits flow proximally past cuff 2 of anesthetic liquid sufficient to increase the concentration of anesthetic liquid to a concentration near a preassigned concentration. Processor 18 also monitors the anesthetic concentration signal and produces an audio-visual alarm signal to the user by means of display 66 on panel 62 if the anesthetic concentration signal exceeds a preassigned concentration safety limit. In practice, processor 18 accomplishes this by monitoring the SRC signal from signal conditioner 60 and producing an alarm signal if the amplitude of the SRC exceeds a predefined threshold, and by monitoring the ECG signal from signal conditioner 58 and producing an alarm signal if the rate of the ECG decreases by more than 15 beats per minute.

It is to be understood that the invention is not to be limited to the details, herein given but may be modified within the scope of the appended claims.

I claim:

1. Apparatus for monitoring the administration of liquid anesthesia in a portion of a patient's limb distal to a cuff, comprising in combination:
   (a) applied pressure transducing means for generating an applied pressure signal representative of a pressure applied to a limb by a cuff which encircles the limb and applies pressure to the limb;
   (b) anesthetic pressure sensing means for sensing the pressure of anesthetic liquid in a vein distal to the cuff and for generating an anesthetic liquid pressure signal indicative of the pressure;
   (c) alarm mean for determining the difference between the pressures corresponding to the applied pressure signal and the anesthetic liquid pressure signal, for comparing the difference therebetween to a preassigned safety limit, and for producing an alarm signal when the difference is less than the preassigned safety limit; and
   anesthetic delivery means for introducing anesthetic liquid into the vein in the limb, the anesthetic delivery means being responsive to the alarm signal for stopping the introduction of anesthetic liquid when the alarm signal is produced.

2. Apparatus for administering anesthesia in a portion of a patient's limb distal to a cuff, comprising in combination:
   (a) a cuff for encircling a limb and applying pressure to the encircled limb to restrict flow past the cuff proximally of liquid in a vein in the portion of the limb distal to the cuff;

(b) applied pressure transducing means for generating an applied pressure signal representative of a pressure applied to the vein by the cuff;

(c) anesthetic delivery means for introducing anesthetic liquid into the vein distal to the cuff and for generating a delivery pressure signal indicative of the pressure at which the liquid is introduced into the vein; and (d) alarm means for determining the difference between the pressures corresponding to the applied pressure signal and the delivery pressure signal, for comparing the difference therebetween to a preassigned safety limit, and for producing an alarm signal when the difference is less than the preassigned safety limit.

3. Apparatus for controlling the containment and release of anesthetic liquid in a vein of a patient's limb distal to a pressurizing cuff comprising:

(a) a pressurizing cuff for substantially encircling a limb and applying pressure to a vein in the encircled limb to restrict flow past the cuff proximally of anesthetic liquid contained in a vein from the portion of the limb distal to the cuff;

(b) anesthetic concentration sensing means for estimating the concentration of anesthetic liquid in blood and for producing an anesthetic concentration signal indicative of the concentration; and (c) cuff pressure control means responsive to the anesthetic concentration signal for controlling the pressure applied by the cuff to the limb.

4. Apparatus as defined in claim 3, and including alarm means for comparing the concentration represented by the anesthetic concentration signal to a preassigned concentration safety limit and for generating an alarm signal when the concentration exceeds the concentration safety limit.

5. Apparatus as defined in claim 3, wherein the anesthetic concentration sensing means comprises:

(a) heart rate sensing means for sensing the heart rate of the patient and for producing a heart rate signal indicative of the patient's heart rate;

(b) resistance sensing means for sensing the change in electrical resistance between two electrodes located at predetermined locations on the limb and for producing a resistance change signal representative of the change in electrical resistance; and (c) signal generating means for producing an anesthetic concentration signal which is inversely proportional to the heart rate signal and directly proportional to the resistance change signal.

6. Apparatus as defined in claim 3, wherein the anesthetic concentration sensing means estimates the concentration of anesthetic liquid in blood distal to the cuff.

7. Apparatus as defined in claim 3, wherein the anesthetic concentration sensing means estimates the concentration of anesthetic liquid in blood proximal to the cuff.

8. Apparatus as defined in claim 7, wherein the cuff pressure control means restricts flow proximally past the cuff of anesthetic liquid to maintain the concentration of anesthetic liquid below a preassigned concentration.

9. Apparatus as defined in claim 7, wherein the cuff pressure control means permits flow proximally past the cuff of anesthetic liquid sufficient to increase the concentration of anesthetic liquid to a concentration near a preassigned concentration.

10. Apparatus for establishing a desired level of anesthesia in a portion of a limb, comprising:

(a) a pressurizing cuff for substantially encircling a limb and applying pressure to a vein in the encircled limb to restrict flow past the cuff proximally of liquid in the vein in the portion of the limb distal to the cuff;

b) anesthetic drug delivery means for introducing an anesthetic liquid into a vein distal to the cuff;

(c) anesthetic level estimation means for estimating a level of anesthesia in the limb and for producing an anesthetic level signal representative of the estimated level of anesthesia; and (d) anesthetic control means responsive to the anesthetic level signal for determining the difference between the anesthetic level signal and a reference signal and for producing the anesthetic delivery signal when the difference is determined to be greater than a predetermined difference threshold.

11. Apparatus as defined in claim 10 and including anesthetic level alarm means responsive to the anesthetic level signal for comparing the level of anesthesia represented by the anesthetic level signal to a preassigned safety limit and for producing an anesthetic alarm signal when the level of anesthesia exceeds the preassigned safety limit.

12. Apparatus as defined in claim 10, wherein the anesthetic level estimation means estimates a level of anesthesia in the portion of the limb proximal to the cuff.

13. Apparatus as defined in claim 10, wherein the anesthetic level estimation means estimates a level of anesthesia in the portion of the limb distal to the cuff.

14. Apparatus as defined in claim 13, wherein the anesthetic level estimation means comprises:

(a) stimulating means for stimulating the limb at a first predetermined location on the limb at a predetermined stimulus time;

(b) detecting means to be positioned at a second predetermined location on the limb for producing a stimulation response signal representative of both the magnitude and the delay in time from the predetermined stimulus time of the response of the limb at the second predetermined location to the stimulating means; and (c) signal generating means responsive to the stimulation response signal for producing an anesthetic level signal which is inversely proportional to the magnitude of the response and which is directly proportional to the delay in time from the predetermined stimulus time of the response of the limb at the second predetermined location to the stimulating means.

15. Apparatus for controlling the containment and release of anesthetic liquid in a vein of a patient's limb, comprising:

(a) pressure application means for applying pressure to a vein in a limb to restrict flow proximally past the pressure application means of anesthetic liquid contained in the vein in the portion of the limb distal to the pressure application means;

(b) anesthetic concentration sensing means for estimating the concentration of anesthetic liquid in blood proximal to the cuff and for producing an anesthetic concentration signal indicative of the concentration; and (c) applied pressure control means responsive to the anesthetic concentration signal for controlling the pressure applied by pressure application means to the vein in the limb.

16. Apparatus as defined in claim 15, wherein the applied pressure control means restricts flow proximally past the pressure application means of anesthetic liquid in order to maintain the concentration represented by the anesthetic concentration signal below a preassigned concentration.

17. Apparatus as defined in claim 15, wherein the applied pressure control means permits flow proximally past the pressure application means of anesthetic liquid sufficient to increase the concentration of anesthetic liquid to a concentration near a preassigned concentration.

18. Apparatus as defined in claim 15, and including alarm means for comparing the concentration represented by the anesthetic concentration signal to a preassigned concentration safety limit and for generating an alarm signal when the concentration exceeds the concentration safety limit.

* * * * *

UNITED STATES PATENT AND TRADEMARK OFFICE
CERTIFICATE OF CORRECTION

PATENT NO. : 5,352,195
DATED : October 4, 1994
INVENTOR(S) : James A. McEwen

It is certified that error appears in the above-indentified patent and that said Letters Patent is hereby corrected as shown below:

On the title page,
In the References Cited:

On page 2, under OTHER PUBLICATIONS, "Hoel" should be -Noel--.

Column 1, line 39, "ststem" should be --system--;

Column 3, line 39, "in" should be --is--; and

Column 4, line 26, "a" (second occurrence) should be --of a--.

Signed and Sealed this

Eleventh Day of April, 1995

Attest:

BRUCE LEHMAN

Attesting Officer

Commissioner of Patents and Trademarks